United States Patent [19]

Nappa et al.

[11] Patent Number: 5,258,561
[45] Date of Patent: Nov. 2, 1993

[54] CATALYTIC CHLOROFLUORINATION PROCESS FOR PRODUCING $CF_3CHClF$ AND $CF_3CHF_2$

[75] Inventors: Mario J. Nappa, Newark; V. N. Mallikarjuna Rao, Wilmington, both of Del.

[73] Assignee: E. I. Du Pont de Nemours and Company, Wilmington, Del.

[21] Appl. No.: 973,015

[22] Filed: Nov. 6, 1992

[51] Int. Cl.$^5$ ............... C07C 17/10; C07C 19/08
[52] U.S. Cl. ............... 570/169; 570/134; 570/135; 570/156; 570/157; 570/161; 570/168
[58] Field of Search ............... 570/134, 135, 156, 161, 570/169, 168, 157

[56] References Cited

U.S. PATENT DOCUMENTS

| | | | |
|---|---|---|---|
| 3,377,287 | 4/1968 | Kvalnes et al. | 570/134 |
| 3,755,477 | 8/1973 | Firth et al. | 570/178 |
| 4,110,407 | 8/1978 | Anello et al. | 570/160 |
| 4,129,603 | 12/1978 | Bell | 570/204 |
| 4,158,675 | 6/1979 | Potter | 570/204 |
| 4,792,643 | 12/1988 | Sobolev | 570/134 |
| 5,036,036 | 7/1991 | Lerou | 502/317 |
| 5,043,491 | 8/1991 | Webster et al. | 570/157 |
| 5,057,634 | 10/1991 | Webster et al. | 570/157 |
| 5,068,472 | 11/1991 | Webster et al. | 570/156 |
| 5,177,273 | 1/1993 | Bruhnke et al. | 570/169 |

FOREIGN PATENT DOCUMENTS

| | | |
|---|---|---|
| 1578933 | 5/1977 | United Kingdom . |
| 2030981B | 8/1978 | United Kingdom . |

*Primary Examiner*—Werren B. Lone

[57] ABSTRACT

A chlorofluorination process is disclosed which employs a catalyst comprising chromium oxide for producing halohydrocarbons of the formula $CHXFCF_3$ (where X is selected from Cl and F). The process is characterized by feeding a combination of components comprising, (i) at least one halohydrocarbon starting compound of the formula $CY_3CH_2R^1$ (where $R^1$ is selected from the group of H and F and each Y is independently selected from the group of Cl and F), (ii) hydrogen fluoride and (iii) chlorine to a reaction zone; contacting said combination of compounds in said reaction zone with a catalyst comprising chromium oxide at an elevated temperature to produce reaction zone products containing halohydrocarbon reaction products of the formula $CHXFCF_3$ together with halohydrocarbons of the formula $CZ_3CHR^2R^3$ (wherein $R^2$ is selected from the group of H and Cl, $R^3$ is selected from the group of H, Cl and F, and each Z is independently selected from Cl and F); and recovering at least a portion of the reaction products from the reaction zone including at least one halohydrocarbon of the formula $CHXFCF_3$. Optionally, a portion of the reaction zone products can be recycled to the reaction zone; and the combination of components contacted with the catalyst can optionally further comprise at least one halohydrocarbon recycle compound of said formula $CZ_3CHR^2R^3$. The process may be controlled to produce compounds of the formula $CHXFCF_3$ in the recovered reaction products as the major component of the halogen-substituted hydrocarbon reaction products in the recovered reaction products.

9 Claims, No Drawings

5,258,561

CATALYTIC CHLOROFLUORINATION PROCESS FOR PRODUCING CF$_3$CHCLF AND CF$_3$CHF$_2$

FIELD OF THE INVENTION

This invention relates to the catalytic chlorofluorination of halogenated ethanes containing hydrogen, and more particularly to the production of halogenated ethanes containing fluorine by such chlorofluorination.

BACKGROUND

Many processes have been disclosed for the preparation of 2-chloro-1,1,1,2-tetrafluoroethane (i.e., HCFC-124 or CHClFCF$_3$) and pentafluoroethane (i.e., HFC-125 or CHF$_2$CF$_3$). Typical processes are described in GB 1,578,933 and U.S. Pat. No. 3,755,477. GB 1,578,933 suggests hydrodehalogenation of various halogenated ethanes including 2,2-dichloro-1,1,1,2-tetrafluoroethane (i.e., CFC-114a or CCl$_2$FCF$_3$) and pentafluoroethane, to form 1,1,1,2-tetrafluoroethane (i.e., HFC-134a or CH$_2$FCF$_3$) and HCFC-124. U.S. Pat. No. 3,755,477 discloses a process for producing fluorinated aliphatic hydrocarbons which comprises fluorinating a halogenated aliphatic hydrocarbon (e.g., 1,1,1-trichloroethane or trichloroethylene) using a gas phase reaction with hydrogen fluoride in the presence of a chromium oxide catalyst. Example 23 therein illustrates using tetrachloroethylene as a raw material, with formation of 20% 2,2-dichloro-1,1,1-trifluoroethane (i.e., CHCl$_2$CF$_3$ or HCFC-123), 20% HCFC-124, 30% HFC-125 and 20% chloropentafluoroethane (i.e., CClF$_2$CF$_3$ or CFC-115).

It is difficult to predict the supply/demand situation for any given hydrofluorocarbon, hydrochlorofluorocarbon or their precursors. There is thus an incentive for develcping numerous routes to commercially valuable hydrofluorocarbons and hydrochlorofluorocarbons. HFC-125 and HCFC-124 are useful as refrigerants, blowing agents, fire extinguishants and propellants. Therefore, there is continuing interest in developing efficient methods of producing these materials.

SUMMARY OF THE INVENTION

The present invention provides a process which employs a catalyst comprising chromium oxide for producing halohydrocarbons of the formula CHXFCF$_3$ (where X is selected from Cl and F). The process is characterized by feeding a combination of components comprising, (i) at least one halohydrocarbon starting compound of the formula CY$_3$CH$_2$R$^1$ (where R$^1$ is selected from the group of H and F and each Y is independently selected from the group of Cl and F), (ii) hydrogen fluoride and (iii) chlorine to a reaction zone; contacting said combination of compounds in said reaction zone with a catalyst comprising chromium oxide at an elevated temperature to produce reaction zone products containing halohydrocarbon reaction products of the formula CHXFCF$_3$ together with halohydrocarbons of the formula CZ$_3$CHR$^2$R$^3$ (wherein R$^2$ is selected from the group of H and Cl, R$^3$ is selected from the group of H, Cl and F, and each Z is independently selected from Cl and F); and recovering at least a portion of the reaction products from the reaction zone including at least one halohydrocarbon of the formula CHXFCF$_3$. Optionally, a portion of the reaction zone products can be recycled to the reaction zone; and the combination of components contacted with the catalyst can optionally further comprise at least one halohydrocarbon recycle compound of the formula CZ$_3$CHR$^2$R$^3$.

Advantageous embodiments of the process include providing a contact time and temperature in the reation zone and an amount of recycle of halohydrocarbons of the formula CZ$_3$CHR$^2$R$^3$ to the reaction zone sufficient to produce halohydrocarbon compounds of the formula CHXFCF$_3$ in the recovered reaction products as the major component of the halogen-substituted hydrocarbon reaction products in the recovered reaction products.

DETAILS OF THE INVENTION

The present invention provides a process for catalytically chlorofluorinating halohydrocarbons of the formula CY$_3$CH$_2$R$^1$, where R$^1$ is selected from the group of H and F and each Y is independently selected from the group of Cl and F (e.g., CH$_3$CCl$_3$, CH$_3$CCl$_2$F, CH$_3$CClF$_2$, CH$_3$CF$_3$, CH$_2$FCCl$_3$, CH$_2$FCCl$_2$F, CH$_2$FCClF$_2$ and/or CH$_2$FCF$_3$) to produce CF$_3$CHClF and/or CF$_3$CHF$_2$.

In accordance with this invention, at least one halohydrocarbon starting compound of the formula CY$_3$CH$_2$R$^1$, and hydrogen fluoride and chlorine are contacted with a catalyst comprising chromium oxide at elevated temperature to produce CHClFCF$_3$ and CHF$_2$CF$_3$. Preferably, the catalyst consists essentially of chromium oxide. Most preferably the catalyst consists essentially of chromium oxide prepared as described in U.S. Pat. No. 5,036,036, which is hereby incorporated by reference herein in its entirety. This includes catalyst compositions comprising Cr$_2$O$_3$ prepared by pyrolysis of (NH$_4$)$_2$Cr$_2$O$_7$ and having an alkali metal content of about 100 ppm or less.

The catalysts of this invention facilitate obtaining high yields of the desired products. Preferably, halohydrocarbon starting compounds of the formula CY$_3$CH$_2$R$^1$ are converted to provide 2-chloro-1,1,1,2-tetrafluoroethane, pentafluoroethane or in some embodiments, a combination of 2-chloro-1,1,1,2-tetrafluoroethane and pentafluoroethane in total, as the major (i.e., about 50 mole percent or more) chlorofluorination product. Most preferably, the chlorofluorination is run without substantial isomerization of CF$_3$CHClF or disproportionation of CF$_3$CHClF or CF$_3$CHF$_2$. For embodiments where CF$_3$CHF$_2$ is the major component of the halogen-substituted hydrocarbon reaction products recovered, the halohydrocarbon materials fed to the reaction zone preferably contain no more than four fluorine substituents; and for embodiments where CF$_3$CHClF is the major component of the halogen-substituted hydrocarbon reaction products recovered, the halohydrocarbon materials fed to the reaction zone preferably contain no more than the three fluorine substituents.

The chlorofluorination reaction of the organic starting material may be conducted in the reaction zone of any suitable reactor, such as a fixed bed reactor. It may be done in a batch or continuous mode; and may be conducted in a single reaction vessel or a combination of reaction vessels. The reaction vessel(s) of the reactor should be constructed of materials which are resistant to the corrosive effects of hydrogen fluoride, hydrogen chloride and chlorine, such as Hastelloy TM nickel alloy and Inconel TM nickel alloy.

The reaction may be run with or without recycle of at least one halohydrocarbon of the formula CZ$_3$CHR$^2$R$^3$ (where R$^2$ is selected from the group of H and Cl, R$^3$ is selected from the group of H, Cl, and F, and each Z is independently selected from Cl and F) from the reaction products. Where no recycle is practiced the halohydrocarbon(s) fed to the reaction zone typically consist essentially of one or more compounds of the formula $CY_3CH_2R^1$. Where recycle is practiced the halohydrocarbons fed to the reaction zone typically include at least one compound of said formula $CZ_3CHR^2R^3$.

The molar ratio of chlorine to the total moles of $CY_3CH_2R^1$ starting compounds and $CZ_3CHR^2R^3$ recycle compounds fed to the reaction zone is typically within the range of from 0.7:1 to 11:1, and is preferably from 1.5:1 to 5:1.

The mole ratio of hydrogen fluoride to the total moles of $CY_3CH_2R^1$ starting compounds and $CZ_3CHR^2R^3$ recycle compounds fed to the reaction zone is typically within the range of from 1:1 to 13:1, and is preferably from 2.9:1 to 7:1.

An inert diluent such as argon, helium or nitrogen may be used in the chlorofluorination reaction of the present invention. If desired oxygen may be cofed into the reaction zone. The molar ratio of oxygen which may be present during the reaction to the total moles of $CY_3CH_2R^1$ and additional recycle, if any, can vary but will typically be within the range of from 0.001:1 to 1:1. The oxygen may be fed to the reaction zone as such or may be diluted with an inert gas such as nitrogen, helium or argon. The source of the oxygen may also be air. The combination of components fed to the reaction zone (i.e., the $CY_3CH_2R^1$, $Cl_2$, HF, and where applicable, other components such as the $CZ_3CHR^2R^3$, oxygen, and/or inert diluents) may be added individually or as mixtures of two or more of the components.

The reaction is conducted at elevated temperature. Generally, the reaction temperature ranges from 200° to 375° C. and is preferably from about 240° to 310° C. The contact time generally will be from about 1 to 60 seconds, and is preferably from about 15 to 30 seconds. Although the chlorofluorination reaction of the present invention is usually conducted at atmospheric pressure, it may also be conducted under elevated or reduced pressure.

2-Chloro-1,1,1,2-tetrafluoroethane and pentafluoroethane in the gaseous mixture discharged from the reactor may be isolated by conventional means, such as distillation. Products of the chlorofluorination reaction of the formula $CZ_3CHR^2R^3$ (e.g., $CHCl_2CF_3$ and/or $CH_2ClCF_3$) may be recycled to the chlorofluorination reaction zone to afford additional HCFC-124 and HFC-125. It is preferred that the halohydrocarbon materials fed to the reaction zone have at least two hydrogen substituents.

HF may be present in some embodiments of the invention as an azeotrope or a mixture of azeotropes. Azeotropic compositions containing HF and $CZ_3CHR^2R^3$ may also be recycled to the reactor.

Practice of the invention will become further apparent from the following non-limiting examples.

EXAMPLE 1

Chlorofluorination of $CH_2FCF_3$

A 15 in. (38.1 cm) × ⅜ in. (0.95 cm) Hastelloy ™ nickel alloy tube was filled with 15.87 g of 12 to 20 mesh (1.7 to 0.84 mm) fresh chrome oxide. The catalyst was activated by heating at 450° C. for 1 hour under a nitrogen purge (50 sccm, $8.3 \times 10^{-7}$ m$^3$/s), then cooled to 300°C. and purged with HF (20 sccm, $3.3 \times 10^{-7}$ m$^3$/s). The flow of HF was then raised to 140 sccm ($2.3 \times 10^{-6}$ m$^3$/s) for 1 hour. The catalyst bed was cooled to 270° C. and $CH_2FCF_3$, HF and $Cl_2$ were fed at 4.0 sccm ($6.7 \times 10^{-8}$ m$^3$/s), 9.0 sccm ($1.5 \times 10^{-7}$ m$^3$/s) and 17.8 sccm ($3.0 \times 10^{-7}$ m$^3$/s), respectively, The reactor effluent had a molar composition as shown in Table 1.

The reactor effluent was sampled on-line with a Hewlett Packard HP 5880 gas chromatograph using a 20 foot long, one-eighth inch diameter, column containing Krytox ™ perfluorinated polyether on an inert support and a helium flow of 35 cc/minute. Gas chromatographic conditions were 70° C. for three minutes followed by temperature programming to 180° C. at a rate of 6° C./minute.

TABLE 1

| % 134a[a] | % 124[b] | % 125[c] | % 123[d] | % 114a[e] | % 113[f] | % 133a[g] | % 114[h] | % 115[i] |
|---|---|---|---|---|---|---|---|---|
| 8.8 | 31.7 | 16.2 | 13.8 | 6.6 | 9.3 | 5.2 | 7.2 | 1.2 |

[a]134a = $CH_2FCF_3$
[b]124 = $CHClFCF_3$
[c]125 = $CHF_2CF_3$
[d]123 = $CHCl_2CF_3$
[e]114a = $CCl_2FCF_3$
[f]113 = $CCl_2FCClF_2$
[g]133a = $CH_2ClCF_3$
[h]114 = $CClF_2CClF_2$
[i]115 = $CClF_2CF_3$

HCFC-123 and HCFC-133a, after removal from the product mixture by distillation, may be recycled to the reaction zone to afford additional HCFC-124 and HFC-125.

EXAMPLE 2

Chlorofluorination of $CH_2FCF_3$

A chrome oxide catalyst prepared as described in Example 1 was used. The catalyst bed was cooled to 298° C. and $CH_2FCF_3$, HF and $Cl_2$ were fed at 1.8 sccm ($3.0 \times 10^{-8}$ m$^3$/s), 12.3 sccm ($2.0 \times 10^{-7}$ m$^3$/s) and 8.9 sccm ($1.5 \times 10^{-7}$ m$^3$/s), respectively. The reactor effluent had a molar composition as shown in Table 2.

TABLE 2

| %125 | %123 | %114a | %113 | %133a | %114 | %115 |
|---|---|---|---|---|---|---|
| 55.5 | 2.2 | 6.3 | 0.2 | 3.1 | 23.3 | 9.2 |

It is understood that the invention is not confined to the particular formulations and examples herein illustrated, but it embraces such modified forms thereof as come within the scope of claims which follow.

What is claimed is:

1. A process for producing halohydrocarbon compounds of the formula $CHXFCF_3$ when X is selected from the group consisting of Cl and F, characterized by:
   (a) feeding a combination of components comprising
       (i) at least one halohydrocarbon starting compound of the formula $CY_3CH_2R^1$ wherein $R^1$ is selected from the group consisting of H and F and each Y is independently selected from the group consisting of Cl and F, (ii) $Cl_2$, (iii) HF and optionally, (iv) at least one recycle compound of the formula $CZ_3CHR^2R^3$ wherein $R^2$ is selected from the group consisting of H and Cl, $R^3$ is selected from the group consisting of H, Cl and F, and each Z is independently selected from the group consisting of Cl and F, to a reaction zone;
   (b) contacting said combination of components in said reaction zone with a catalyst composition comprising a catalytically effective amount of chromium oxide or HF-activated chromium oxide at a temperature of at least about 200° C. to produce reaction zone products containing halohydrocarbon reaction products of the formula $CHXFCF_3$ together with halohydrocarbons of the formula $CZ_3CHR^2R^3$;

(c) recovering at least a portion of the reaction zone products from the reaction zone including at least one halohydrocarbon of the formula $CHXFCF_3$;

(d) optionally recycling a portion of the reaction products to said reaction zone; and (e) providing a catalyst contact time and temperature in said reaction zone and an amount of recycle of halohydrocarbons of the formula $CZ_3CHR^2R^3$ to said reaction zone sufficient to produce halohydrocarbon compounds of the formula $CHXFCF_3$ in said recovered reaction products as the major component of the halogen-substituted hydrocarbon reaction products in said recovered reaction products.

2. The process of claim 1 wherein the reaction temperature is within the range of from 200° C. to 375° C.; wherein the molar ratio of $Cl_2$ to the total moles of $CY_3CH_2R^1$ starting compounds and $CZ_3CHR^2R^3$ recycle compounds in said combination of components fed to the reaction zone is within the range of from 0.7:1 to 11:1; and wherein the molar ratio of HF to the total moles of $CY_3CH_2R^1$ starting compounds and $CZ_3CHR^2R^3$ recycle compounds in said combination of components fed to the reaction zone is within the range of from 1:1 to 13:1.

3. The process of claim 2 wherein the catalyst consists essentially of chromium oxide.

4. The process of claim 2 wherein the catalyst comprises $Cr_2O_3$ prepared by the pyrolysis of $(NH_4)_2Cr_2O_7$ and having an alkali metal content of about 100 ppm or less.

5. The process of claim 2 wherein the halohydrocarbon starting compound is $CH_2FCF_3$.

6. The process of any one of claims 2 through 5 wherein the $CF_3CHF_2$ is the major component of the halogen-substituted hydrocarbon reaction products recovered.

7. The process of claim 6 wherein the halohydrocarbon materials fed to the reaction zone contain no more than four fluorine substituents.

8. The process of any one of claims 2 through 5 wherein a combination of $CF_3CHF_2$ and $CF_3CHClF$ in total is the major component of the halogen-substituted hydrocarbon reaction products recovered.

9. The process of any one of claims 2 through 4 wherein $CF_3CHClF$ is the major component of the halogen-substituted hydrocarbon reaction products recovered; and wherein the halohydrocarbon materials fed to the reaction zone contain no more than three fluorine substituents.

* * * * *